United States Patent [19]

Shaw et al.

[11] 4,338,521
[45] Jul. 6, 1982

[54] MODULAR RADIATION DETECTOR ARRAY AND MODULE

[75] Inventors: R. Howard Shaw, Palo Alto; Charles C. Morehouse, Cupertino, both of Calif.

[73] Assignee: General Electric Company, Milwaukee, Wis.

[21] Appl. No.: 148,261

[22] Filed: May 9, 1980

[51] Int. Cl.³ .............................................. G01T 1/20
[52] U.S. Cl. ..................................... 250/366; 250/367
[58] Field of Search ................... 250/366, 367, 445 T, 250/363 S, 370

[56] References Cited

U.S. PATENT DOCUMENTS

| | | | |
|---|---|---|---|
| 4,037,105 | 7/1977 | Laurer | 250/367 |
| 4,069,421 | 1/1978 | Bourdel | 250/363 S |
| 4,075,491 | 2/1978 | Boyd | 250/445 T |
| 4,085,327 | 4/1978 | Swank et al. | 250/370 |
| 4,181,856 | 1/1980 | Bone | 250/367 X |
| 4,187,427 | 2/1980 | Cusano | 250/367 X |
| 4,190,772 | 2/1980 | Dinwiddie et al. | 250/445 T |

Primary Examiner—Davis L. Willis
Attorney, Agent, or Firm—Dana F. Bigelow; Douglas E. Stoner

[57] ABSTRACT

A modular radiation detector array which allows improved spatial resolution and facilitates installation and replacement for repair. Each module includes two detachably assembled portions with one portion including a plurality of spaced plates for collimating radiation. The second portion includes a printed circuit board, a semiconductor diode array chip mounted on the printed circuit board, and a plurality of scintillator crystals mounted on the semiconductor chip with each crystal overlying a diode. Signals from the diodes are applied to signal processing means by a cable which is readily connected to and disconnected from the diode array.

19 Claims, 8 Drawing Figures

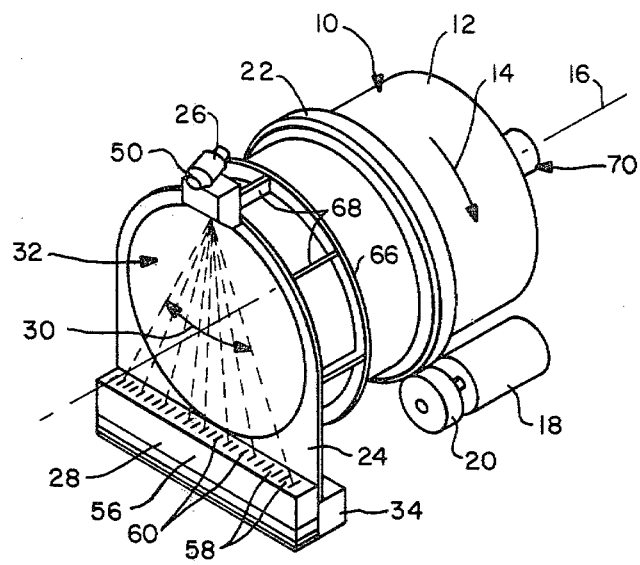
FIG.—1
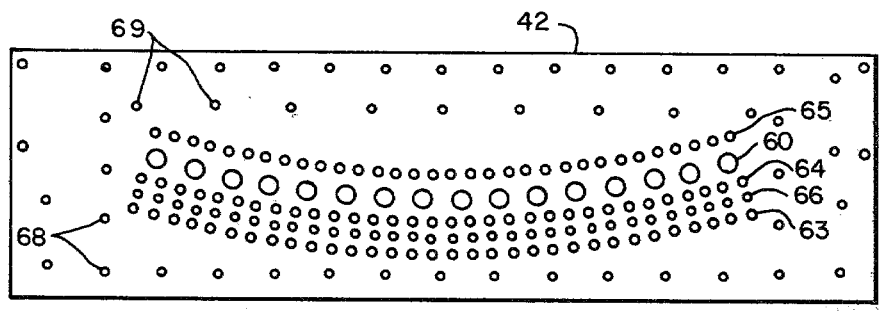
FIG.—5

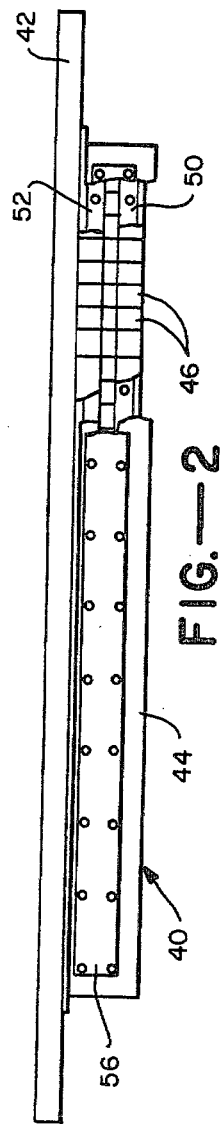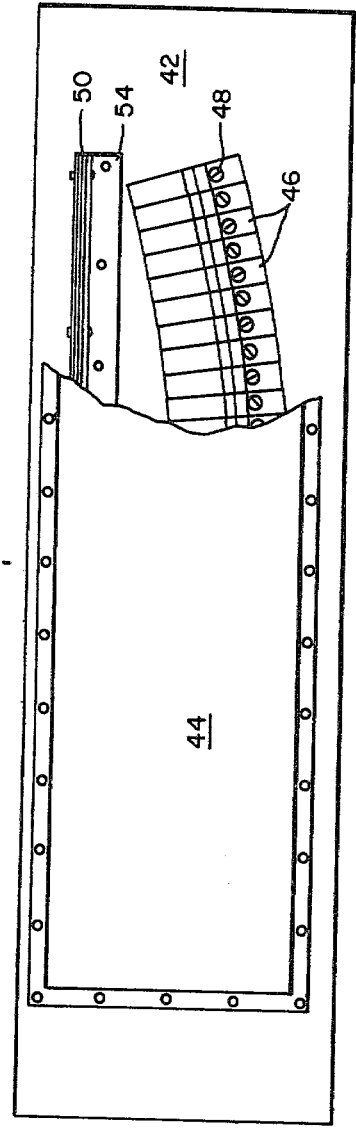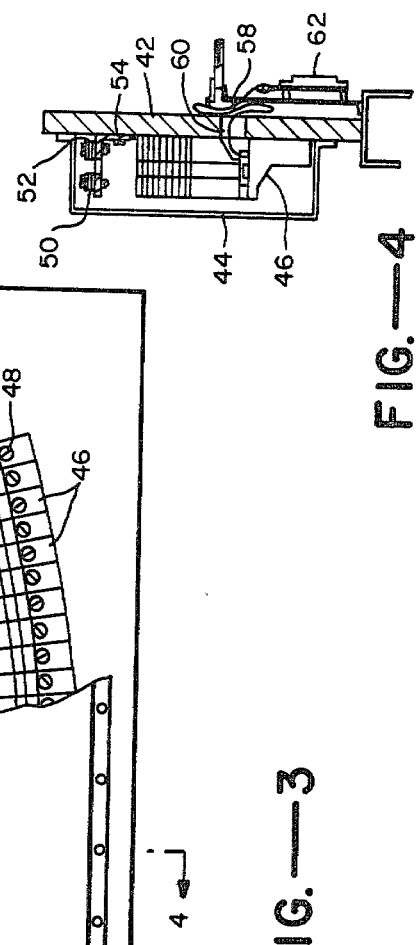

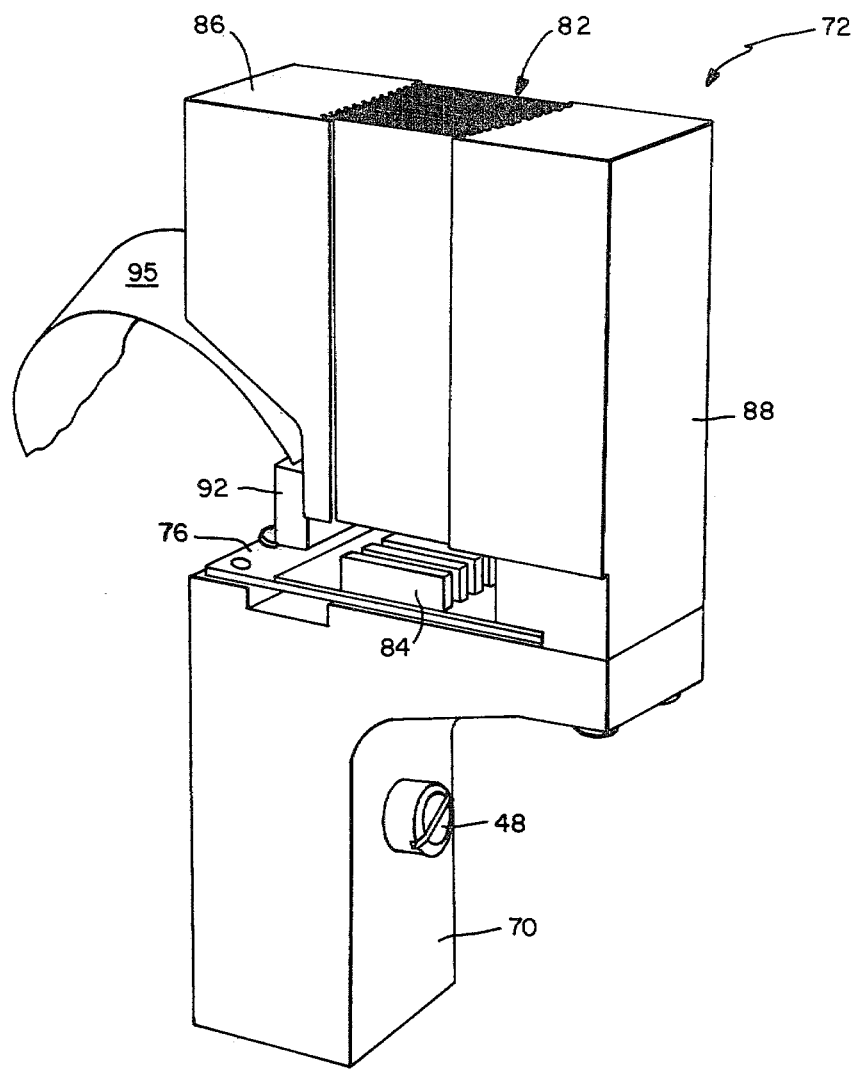
FIG.—6

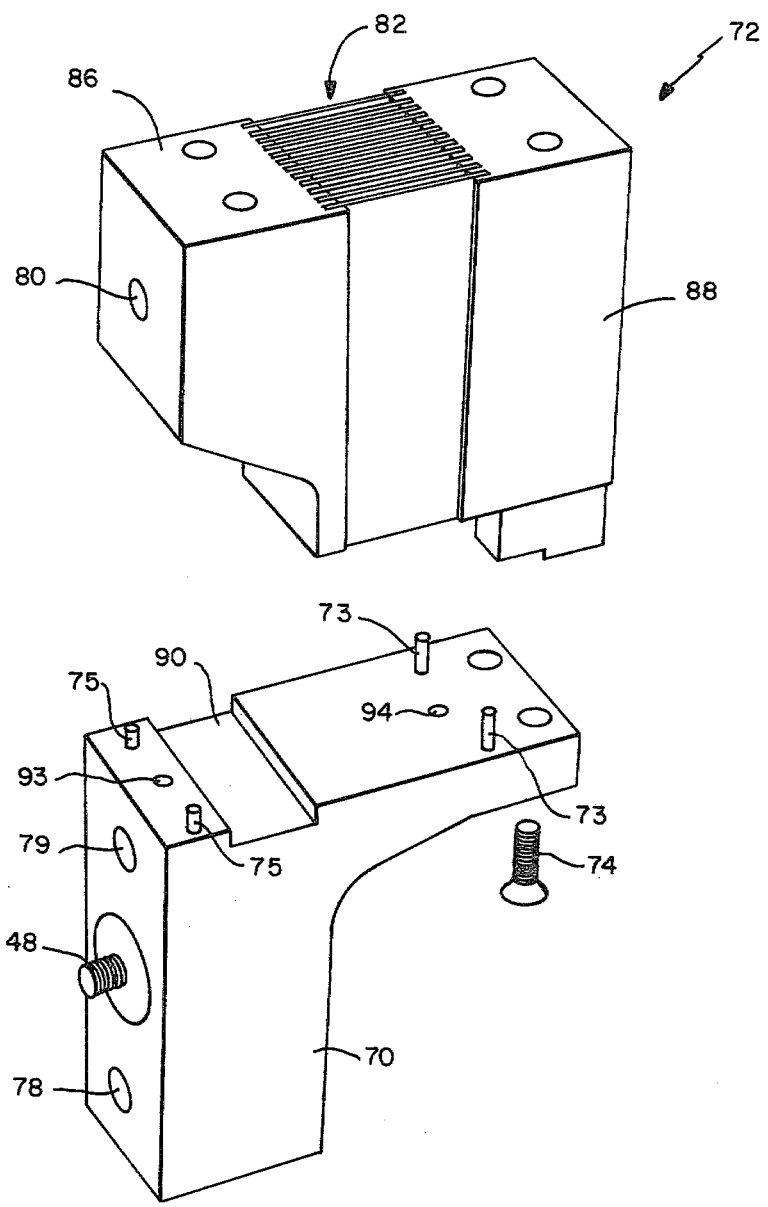
FIG.—7

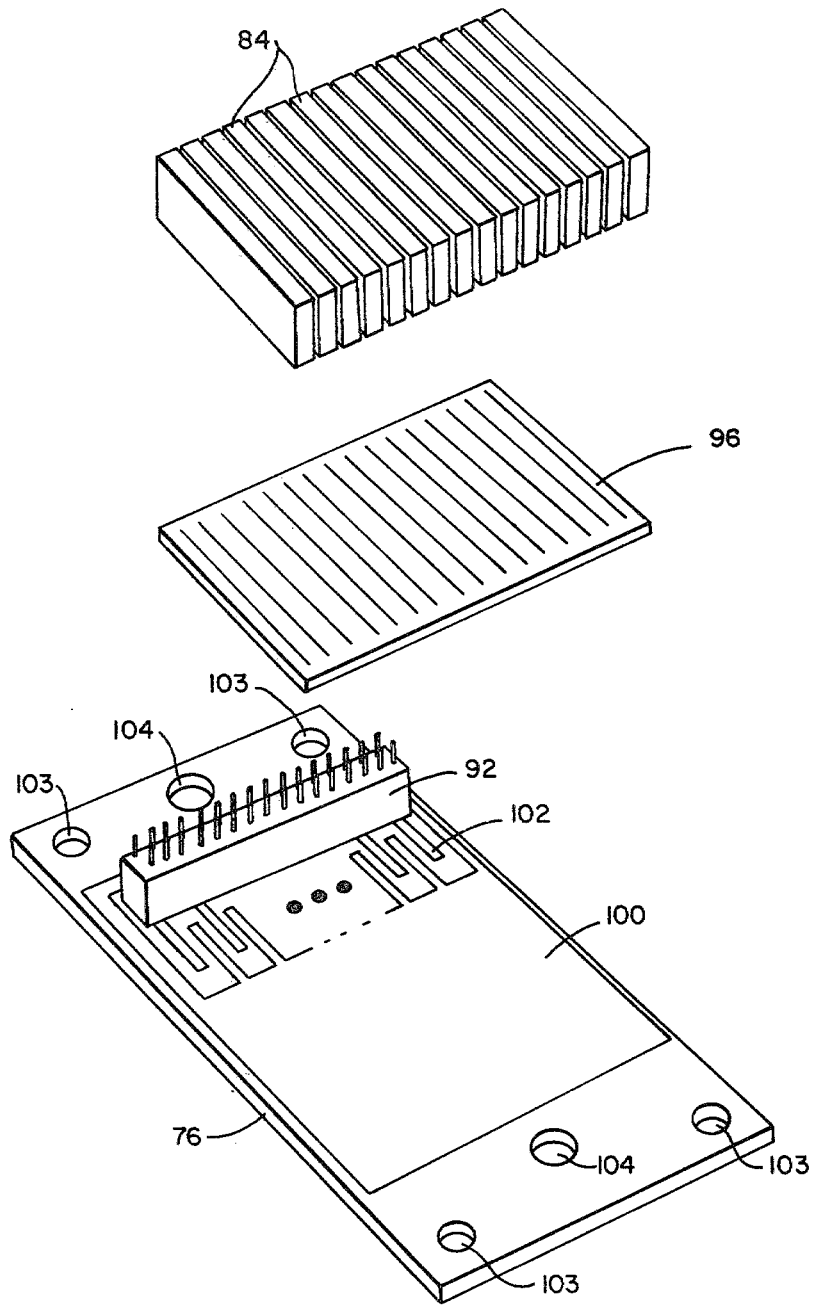
FIG.—8

MODULAR RADIATION DETECTOR ARRAY AND MODULE

This invention relates generally to radiation detectors, such as used in X-ray scanning apparatus, and more particularly the invention relates to a modular radiation detector array.

In computerized tomography an X-ray scanning apparatus is employed to direct a divergent fan beam of radiation through a patient with the penetrating radiation being received by a radiation detector positioned opposite from the radiation source. Typically, the radiation source and detector are rotated about the patient and shadowgram or projection data is obtained at a plurality of angularly spaced positions. The shadowgram data is then reconstructed by computer means to obtain a tomograph of the irradiated section of the patient.

U.S. Pat. No. 4,075,491 and U.S. Pat. No. 4,190,772 disclose tomographic scanning apparatus in which the radiation source and the radiation detector are rotatably mounted to scan a patient at a plurality of angularly displaced positions. In order to get multiple position scans for a fixed position of the radiation source, shifter means is employed to physically adjust the position of the detector on the tomographic apparatus. In both patents the detector is a unitary structure such as a xenon filled chamber with a plurality of anode and cathode structures arranged to define detector elements. The use of crystal scintillators with photomultipliers or photodiodes for the elements in the unitary structure is suggested in the '772 patent.

The radiation detectors heretofore proposed have several limitations. The unitary structures are heavy and difficult to handle during assembly and in shifting the detector position to obtain multiple position scanning. Modification of the detector array configuration is limited due to the unitary structure. Further, the failure of any one detector element requires replacement of the entire detector, and repair of the defective element is compounded by the unitary structure.

Accordingly, an object of the present invention is an improved radiation detector array.

Another object of the invention is a radiation detector array with improved radiation absorption and detection efficiency.

Another object of the invention is a detector array which is easily installed and readily modified in configuration.

Still another object of the invention is a modular detector array and detector module which facilitate maintenance.

Yet another object of the invention is a radiation detector module which is easily repaired.

Briefly, in accordance with the invention a modular detector array comprises a plurality of detector modules whereby any defective module can be readily replaced without affecting the operability of the detector array. Because of the modularity of the array, installation and positioning of the array in the tomographic apparatus is facilitated.

Each module of the array includes a plurality of photodiodes and a plurality of scintillator crystals with each scintillator crystal cooperatively arranged with one of the photodiodes whereby radiation received by a scintillator crystal generates photons which are transmitted to one of the photodiodes. Each module may also include a printed circuit board, means attaching the plurality of photodiodes to the printed circuit board, and an electrical connector mounted on the printed circuit board with means electrically interconnecting the plurality of photodiodes to the connector. Thus, the module is readily connected and disconnected in the array.

A radiation beam collimator can be provided in cooperative arrangement with the scintillator crystals whereby the collimator directs collimated radiation to each scintillator crystal.

In a preferred embodiment the module comprises a first portion in which is mounted the printed circuit board, diode array, and scintillator crystals. A second portion including the collimator is detachably assembled with the first portion with the two assembled portions being readily mounted to the tomographic apparatus.

The invention and objects and features thereof will be more readily apparent from the following detailed description and appended claims when taken with the drawing, in which:

FIG. 1 is a perspective view of tomographic scanning apparatus.

FIG. 2 is a top view of one embodiment of a modular detector array in accordance with the present invention.

FIG. 3 is a front view of the modular detector array of FIG. 2.

FIG. 4 is a side view in section of the modular detector array of FIGS. 2 and 3.

FIG. 5 is a front view of the base plate on which the modular detector array of FIGS. 2-4 is mounted.

FIG. 6 is a perspective view of one embodiment of a detector module in accordance with the present invention.

FIG. 7 is an exploded perspective view illustrating detached portions of the detector module of FIG. 6.

FIG. 8 is an exploded perspective view of the scintillator crystals, photodiode, and printed circuit board of one portion of the module of FIG. 6.

The same reference numerals are used for like components in the several views of the modular detector array and module.

Referring now to the drawings, FIG. 1 is a perspective view of tomographic scanning apparatus such as disclosed in U.S. Pat. No. 4,190,772. The apparatus includes a rotatable assembly shown generally at 10 comprising an outer cylinder 12 which is adapted to be rotated in a direction 14 about the central axis 16 by means of a motor 18 and the drive wheel 20 which bears against a drive collar 22 which is secured about the cylinder 12. Mounted on a base plate 24 is a radiation source 26 and a detector 28 which is opposite from source 26. The radiation source 26 projects an X-ray pattern in the form of a fan beam 30 which is received by detector 28.

In operation, a patient is positioned within the central opening 32 between the source 26 and detector 28. By rotating the radiation source 26 and detector 28 about the patient, shadowgram data is obtained at a plurality of angularly displaced positions from which a tomograph of the irradiated section of the patient can be reconstructed by computer techniques.

In prior art apparatus the detector typically comprises a unitary array of ionization chambers such as xenon-crypton detectors which convert the received radiation into electrical signals which are then transmitted to a recorder in the signal processing means 34.

Typically, the detector is relatively heavy which makes assembly and adjustment of the detector on the support plate 24 difficult. Further, being a unitary structure any defective cell requires replacement of the entire detector.

In accordance with the present invention a modular radiation detector array is provided which is more easily installed and maintained. FIGS. 2, 3, and 4, respectively, are a top view, a front view, and a side view of one embodiment of a modular detector array shown generally at 40 which is mounted to a base plate 42 of scanning apparatus. A portion of the cover 44 is removed in each of the views to further illustrate the arrangement of the modules 46 of the array. Each of the modules is attached to base plate 42 by means of a bolt 48 in cooperation with alignment pins extending from base plate 42, as will be described further hereinbelow with reference to FIG. 5.

Positioned above the modular array are a pair of spaced radiation shields 50 and 52 which are mounted to base plate 42 by means of bracket 54. The shields may comprise lead with stainless steel facings for strength with the spacing between the two shields defining a fan beam of radiation for transmission to the detector array. The top surface of cover 44 includes an optically opaque wall 56 such as plastic which allows the transmission of radiation but blocks the transmission of light to the enclosed modular detector array.

As shown in FIG. 4 each of the modules 46 is connected by an electrical cable 58, which passes through an opening 60 in the base plate 42, to a connector 62. As will be described further hereinbelow each module is readily connected and disconnected in the scanning apparatus to facilitate assembly and servicing of the modules.

Referring now to FIG. 5, a front view of the base plate 42 is illustrated with the modular detector array removed to further illustrate the mounting of the array to the base plate. The plate includes three rows of alignment pins 63, 64 and 65 with one pin in each row engaging a detector module for alignment and support purposes. The bolt 48 which attaches each of the modules to the base plate mates with a hole in the row 66. Thus, each module is aligned and supported by three pins with a bolt 48 attaching the module to the base plate 42. Openings 60 in the base plate allow the passage of connector cables from each module to the recorder behind the plate. Holes 68 receive screws for mounting cover 44 to the base plate 42, and holes 69 receive screws for mounting of bracket 54 to the base plate 42.

Referring now to FIGS. 6 and 7, perspective views of a detector module are illustrated in assembly and in an exploded view, respectively. The module includes a first portion or base 70 and a second portion 72 which is detachably assembled to the base 70 by means of a pair of alignment pins 73 and bolts 74. Base 70 also includes a second pair of pins 75 which cooperate with pins 73 for receiving and aligning a printed circuit board 76 on which the scintillator crystals 84 and photodiodes are mounted. Printed circuit board 76 is removed in the exploded view of FIG. 7 to further illustrate the support 70. The alignment pins 63, 64, and 65 extending from the base plate 42, as illustrated in FIG. 5, are received respectively by holes 78, 79, and 80 illustrated in FIG. 7. Bolt 48 extends through the support 70 for attaching the assembled module to base plate 42.

Portion 72 of the detector module includes a plurality of spaced plates 82 with adjacent plates defining a path for directing collimated radiation to a scintillator crystal 84 mounted on the printed circuit board 76. The plates 82 can be stainless steel and are permanently affixed in grooves in opposing surfaces of support members 86 and 88 by a suitable epoxy cement such as Shell Epon 815 epoxy. The spacing of plates 82 is correlated with the width of a scintillator crystal 84, and the plates are aligned with the scintillator crystals by the pins 73 and bolts 74 which locate and attach the two assembled portions 70 and 72 of the detector module. While a collimator is employed in the illustrative embodiment use of a collimator is not essential in the detector module.

Groove 90 in the top surface of the base 70 is provided to accommodate the two piece connector 92 mounted on printed circuit board 76, and holes 93 and 94 in the top surface of base 70 receive screws for fastening the printed circuit board 76 on support 70. Ribbon cable 95 extends from the top or female portion of connector 92 and interconnects with the recorder apparatus 34 of FIG. 1.

Referring now to FIG. 8, an exploded perspective view is shown of the printed circuit board 76, photodiode semiconductor chip 96, and scintillator crystals 84. The printed circuit board 76 has a metal pattern including pad 100 and leads 102 defined thereon. The photodiode semiconductor chip 96 is attached to pad 100 by suitable conductive epoxy, and contacts to each of the diodes of the semiconductor chip 96 are wire bonded to the leads 102 to interconnect the photodiodes to the male portion of connector 92. Holes 103 in the printed circuit board 76 receive the alignment pins 73 and 75 of the support 70, as shown in FIG. 7, and holes 104 receive screws which mate with holes 93 and 94 of the base 70 for fastening the printed circuit board to the base. Each scintillator crystal 84 is bonded to the semiconductor chip 96 by a suitable adhesive such as Kodak-HE-80 with each crystal 84 aligned with a photodiode. Each crystal is of suitable dimensions for fully covering a photodiode so that the diode receives photons only from the aligned scintillator crystal.

The photodiode chip 96 comprises an integrated PIN diode structure which can be obtained from commercial semiconductor suppliers such as United Detector Technology, Inc. of Santa Monica, California. The connector can be obtained from AMP, Inc. of Harrisburg, Pennsylvania, and the scintillation crystals are commercially available BGO devices such as manufactured by Crystal Technology, Inc. of Mt. View, California.

In one embodiment sixteen channels were provided in each module with the module having a sixteen diode chip and receiving radiation in one degree of fan beam arc. Because the solid state detector elements are smaller than zenon type detectors, the higher density allows improved spatial resolution as compared with conventional detectors. The modular construction of the detector array allows each module to be readily disconnected from the scanning apparatus for repair and replacement.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A modular detector array for use in detecting radiation in tomographic apparatus and the like comprising a plurality of detector modules, each of said modules comprising a first portion including a plurality of photodiodes and a plurality of scintillator crystals with each of said scintillator crystals cooperatively arranged with one of said photodiodes whereby radiation received by a scintillator crystal generates photons in said scintillator crystal which are transferred to one of said photodiodes, and a second portion including a collimator for directing collimated radiation to a scintillator crystal, said first portion and said second portion being detachably assembled.

2. A modular detector array as defined by claim 1 and further including means for attaching said plurality of detector modules to said tomographic apparatus for detecting a divergent beam of radiation.

3. A modular detector array as defined by claim 2 and further including a cover for enclosing said plurality of modules when attached to said tomographic apparatus and means for selectively transmitting a fan shaped beam of radiation to said plurality of detectors.

4. A modular detector array as defined by claim 3 wherein said means for transmitting a fan shaped beam comprises a pair of spaced radiation shields with said fan shaped beam being defined by the spacing of said radiation shields.

5. A modular detector array as defined by claim 4 wherein said cover includes an optically opaque wall over said pair of spaced radiation shields.

6. A modular detector array as defined by claim 1 wherein said second portion comprises a plurality of spaced apart plates and support means on opposing ends of said plates for maintaining said plates in spaced alignment.

7. A modular detector array as defined by claim 6 wherein adjacent plates define a collimated path for directing radiation to a scintillator crystal.

8. A modular detector array as defined by claim 1 wherein said first portion further includes a printed circuit board, means attaching said plurality of photodiodes to said printed circuit board, an electrical connector mounted on said printed circuit board, and means electrically interconnecting said plurality of photodiodes to said connector.

9. A modular detector array as defined by claim 8 wherein said printed circuit board has a plurality of alignment holes and said first portion further includes a support having a plurality of pins, said support receiving said printed circuit board with said pins engaging said alignment holes.

10. A modular detector array as defined by claim 9 wherein said second portion includes a plurality of holes for mating with pins of said first portion.

11. A modular detector array as defined by claim 1 or 9 and further including means for attaching said plurality of detector modules to said tomographic apparatus for detecting a divergent beam of radiation.

12. A modular detector array as defined by claim 11 and further including a cover for enclosing said plurality of modules when attached to a tomographic apparatus and means for selectively transmitting a fan shaped beam of radiation to said plurality of detectors.

13. A modular detector array as defined by claim 12 wherein said means for selectively transmitting a fan shaped beam comprises a pair of spaced radiation shields whereby said fan shaped beam is defined by the spacing of said radiation shields.

14. A modular detector array as defined by claim 13 wherein said cover includes an optically opaque wall over said pair of spaced radiation shields.

15. A detector module for use in a modular detector array comprising a first portion including a plurality of photodiodes and a plurality of scintillator crystals with each of said scintillator crystals cooperatively arranged with one of said photodiodes whereby radiation received by a scintillator crystal generates photons in said generator crystal which is transmitted to one of said photodiodes, and a second portion including a collimator for directing collimated radiation to each of said plurality of scintillator crystals, said first portion and said second portion being detachably assembled.

16. A detector module as defined by claim 15 wherein said second portion comprises a plurality of spaced apart plates and support means on opposing ends of said plates for maintaining said plates in spaced alignment.

17. A detector module as defined by claim 15 or 16 wherein said first portion further includes a printed circuit board, means attaching said plurality of photodiodes to said printed circuit board, an electrical connector mounted on said printed circuit board, and means electrically interconnecting said plurality of photodiodes to said connector.

18. A detector module as defined by claim 17 wherein said printed circuit board has a plurality of alignment holes and said first portion further includes a support having a plurality of pins, said support receiving said printed circuit board with said pins engaging said alignment holes.

19. A detector module as defined by claim 18 wherein said second portion includes a plurality of holes for mating with pins of said first portion.

* * * * *